(12) United States Patent
Graveley et al.

(10) Patent No.: US 12,239,290 B2
(45) Date of Patent: Mar. 4, 2025

(54) SYSTEMS FOR LIMITING MOVEMENT OF CONTROL MECHANISMS

(71) Applicant: Boston Scientific Scimed, Inc., Maple Grove, MN (US)

(72) Inventors: Andrew Brian Graveley, Indianapolis, IN (US); Ana Marcela Cordero Munoz, Bloomington, IN (US); Leslie Sherwood, Ellettsville, IN (US); Gregory Ostrander, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 462 days.

(21) Appl. No.: 16/922,386

(22) Filed: Jul. 7, 2020

(65) Prior Publication Data

US 2021/0007582 A1     Jan. 14, 2021

Related U.S. Application Data

(60) Provisional application No. 62/871,386, filed on Jul. 8, 2019.

(51) Int. Cl.
*A61B 1/005* (2006.01)
*A61B 1/00* (2006.01)
*A61B 90/00* (2016.01)

(52) U.S. Cl.
CPC ........ *A61B 1/0052* (2013.01); *A61B 1/00098* (2013.01); *A61B 1/0055* (2013.01);
(Continued)

(58) Field of Classification Search
CPC . A61B 1/0052; A61B 1/00098; A61B 1/0055; A61B 1/0057; A61B 90/03; A61B 2090/035; Y10T 137/86823; Y10T 137/86815; Y10T 137/9464; Y10T 74/20732; Y10T 403/7005; Y10T 403/7009; Y10T 403/7011; Y10T 403/7013; F16K 31/006; F16C 1/26; G05G 5/02; G05G 5/28; G05G 2505/00; F16B 21/06
(Continued)

(56) References Cited

U.S. PATENT DOCUMENTS 5,014,685 A  *  5/1991  Takahashi ......... A61M 25/0136
                                                    600/148
2001/0037051 A1* 11/2001  Fujii .................... A61B 1/0052
                                                    600/146
(Continued)

FOREIGN PATENT DOCUMENTS

JP          5045990 U       5/1975
JP       2013005996 A       1/2013

*Primary Examiner* — Aaron B Fairchild
*Assistant Examiner* — Megan Elizabeth Monahan
(74) *Attorney, Agent, or Firm* — Bookoff McAndrews, PLLC

(57) ABSTRACT

An assembly may have an axle. Rotation of the axle may cause deflection of a portion of a medical device. A collet may have an opening. The axle may extent through the longitudinal opening. An actuator may be configured to interact with the collet. A first configuration of the collet may permit rotation of the axle relative to the collet and a second configuration of the collet may inhibit rotation of the axle relative to the collet.

20 Claims, 6 Drawing Sheets

(52) U.S. Cl.
CPC ............ *A61B 1/0057* (2013.01); *A61B 90/03* (2016.02); *A61B 2090/035* (2016.02)

(58) Field of Classification Search
USPC .......... 16/441, 436; 4/695; 137/801, 625.41, 137/625.4; 74/543, 500, 55; 24/273; 403/348–350
See application file for complete search history.

(56) References Cited

U.S. PATENT DOCUMENTS

| | | | |
|---|---|---|---|
| 2006/0252993 A1* | 11/2006 | Freed | A61B 1/0052 604/95.04 |
| 2009/0287188 A1* | 11/2009 | Golden | A61M 25/0147 604/528 |
| 2013/0103001 A1* | 4/2013 | BenMaamer | A61M 25/09 604/528 |
| 2014/0058323 A1* | 2/2014 | Hoshino | G02B 23/2476 604/95.04 |

* cited by examiner

SYSTEMS FOR LIMITING MOVEMENT OF CONTROL MECHANISMS

CROSS-REFERENCE TO RELATED APPLICATIONS

This application claims the benefit of priority from U.S. Provisional Application No. 62/871,386, filed on Jul. 8, 2019, which is incorporated by reference herein in its entirety.

TECHNICAL FIELD

The present disclosure relates generally to systems for limiting movement of control mechanisms. In particular, this disclosure is directed to locking mechanisms for medical devices, such as, for example, devices for locking articulation control knobs of endoscopes.

BACKGROUND

Handles of the medical devices, such as endoscopes, may include control mechanisms, such as knobs. Such control mechanisms may be used to, for example, articulate a sheath of the medical device. During a procedure, an operator may desire to limit articulation of the sheath. For example, an operator may desire to limit articulation when a sheath is inserted into a patient or while a procedure is being performed. Therefore, a need exists for locking mechanisms.

SUMMARY

An assembly may have an axle. Rotation of the axle may cause deflection of a portion of a medical device. A collet may have an opening. The axle may extent through the longitudinal opening. An actuator may be configured to interact with the collet. A first configuration of the collet may permit rotation of the axle relative to the collet and a second configuration of the collet may inhibit rotation of the axle relative to the collet.

Any of the assemblies described herein may have any of the following features. The actuator may include a protrusion. The collet may include a tab. The protrusion may interact with the tab to transition the collet from the first configuration to the second configuration. The protrusion may be a first protrusion. The actuator may further include a second protrusion and a third protrusion. The tab may be a first tab. The collet may further include a second tab and a third tab. The second protrusion and the third protrusion may interact with the second and third tabs, respectively, to transition the collet from the first configuration to the second configuration. A notch in the collet may define a portion of the tab having a reduced length relative to adjacent portions of the tab. The tab may have a first portion and a second portion. The first portion may be less flexible than the second portion. In the first configuration, the protrusion may interact with the first portion. In the second configuration, the protrusion may interact with the second portion. The second portion may have a greater thickness along a radial direction than the first portion. The tab may be biased to an at-rest position when the collet is in the first configuration. A radially-inner surface of the tab may radially aligned with an adjacent portion of the collet or protrudes radially outward from the adjacent portion of the collet. The collet may be transitioned from the first configuration to the second configuration by rotation of the actuator. The actuator may include a lever. The actuator may include a washer-shaped portion. The lever may extend radially outward from the washer-shaped portion. The collet may include a sleeve, and a flange extending circumferentially around at least a portion of the sleeve. The collet may include a stop configured to prevent movement of a portion of the actuator past the stop. The actuator may be radially outward of the collet. Rotation of the actuator may cause the collet to transition from the first configuration to the second configuration. A flexible tab of the collet may apply a frictional force to the axle, when the collet is in the second configuration.

In another example, an assembly may comprise a collet having a flexible tab. and an actuator having a protrusion extending radially inward from a surface of the actuator. The protrusion may interact with the tab to transition the collet from a first configuration to a second configuration. In the first configuration of the collet, an axle may be rotatable to deflect a portion of a medical device. In the second configuration of the collet, the axle may not be rotatable due to a frictional force applied to the axle from the tab.

Any of the assemblies described herein may include any of the following features. The actuator may include a washer-shaped portion. The protrusion may extend from an inner surface of the washer-shaped portion. The tab may be biased to an at-rest position that is radially aligned with an adjacent portion of the collet or protrudes radially outward from the adjacent portion of the collet.

In another example, an assembly may comprise an axle. Rotation of the axle may cause deflection of a sheath of a medical device. A collet may have a sleeve portion. The axle may extend through a central opening of the sleeve portion. The sleeve portion may have a flexible tab. An actuator may have a washer-shaped portion radially outward of the sleeve portion. The actuator may include a protrusion extending radially inward from an inner surface of the washer-shaped portion. The protrusion may be adjacent to at least a portion of the tab.

Any of the assemblies described herein may have any of the following features. The actuator may rotate relative to the collet so that the protrusion applies a radially-inward force on the tab.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The terms "approximately" or "substantially" may be understood as referring to a range of +/−10%. As used herein, the term "proximal" means a direction closer to an operator and the term "distal" means a direction further from an operator. Although endoscopes are referenced herein, reference to endoscopes or endoscopy should not be construed as limiting the possible applications of the disclosed locking mechanisms and other aspects. For example, the disclosed aspects may be used with duodenoscopes, bronchoscopes, gastroscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Handles of endoscopes or other medical devices (e.g., operational portions of endoscopes) may include components that are used by an operator when performing a procedure with the endoscope. As described above, during a procedure, a medical professional may desire to limit articulation of a distal end of an endoscope via complex locking mechanisms or additional devices. Known medical devices may include locking mechanisms to prevent articulation of a sheath and maintain a position or orientation of a distal end of the medical device. Such locking mechanisms may include numerous parts, which may contribute to high costs of manufacture of the medical device. Issues with assembly of multiple-part locking mechanisms also may result in disposal of an improperly assembled medical device after manufacture and before distribution, contributing to waste.

Figure 1:
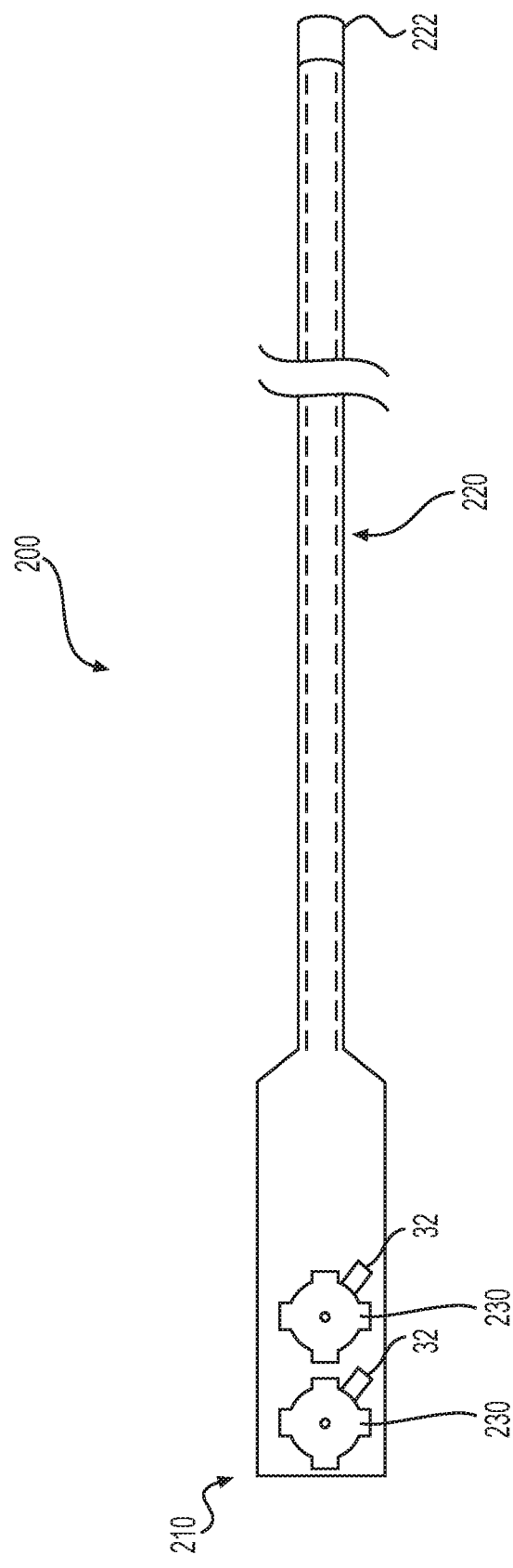
FIG. 1 shows an exemplary endoscope.

Referring now to FIG. 1, a handle 210 of an endoscope 200 may include steering components or assemblies, which may be used to deflect a distal end 222 of a sheath 220 of endoscope 200. Steering components may include knobs, levers, or other mechanisms used to control a steering assembly. For example, one or more steering knobs 230 or levers may be used to articulate sheath 220 in an up/down and or left/right direction. Endoscope handles may also include mechanisms for preventing or limiting unwanted articulation of the sheath (e.g., during insertion or during other portions of a medical procedure). For example, the handle may include one or more brake assemblies 10 (see FIG. 2) that prevent or otherwise limit articulation of the sheath. Brake assembly 10 may include an actuator, such as a lever 32. Brake assembly 10 may be coaxial with knob 230 on, for example, axle 41. The lever 32 may be made of a molded plastic material or other material, such as metal or combinations of materials. The brake assembly 10 may also include a collet that may interact with the lever. In a first configuration of the lock, an axle of a steering assembly may be free to rotate relative to the collet. In a second configuration of the lock, the collet may be tightened about the axle so that the axle is not able to rotate relative to the collet or requires an increased amount of force to rotate, such as an amount of force that would not be exerted by a user of the device in the ordinary course. Alternatively, tightening of the collet about the axle may increase an amount of force required to rotate the axle (increasing a resistance to articulation), while still allowing for rotation about the axle.

Figure 2:
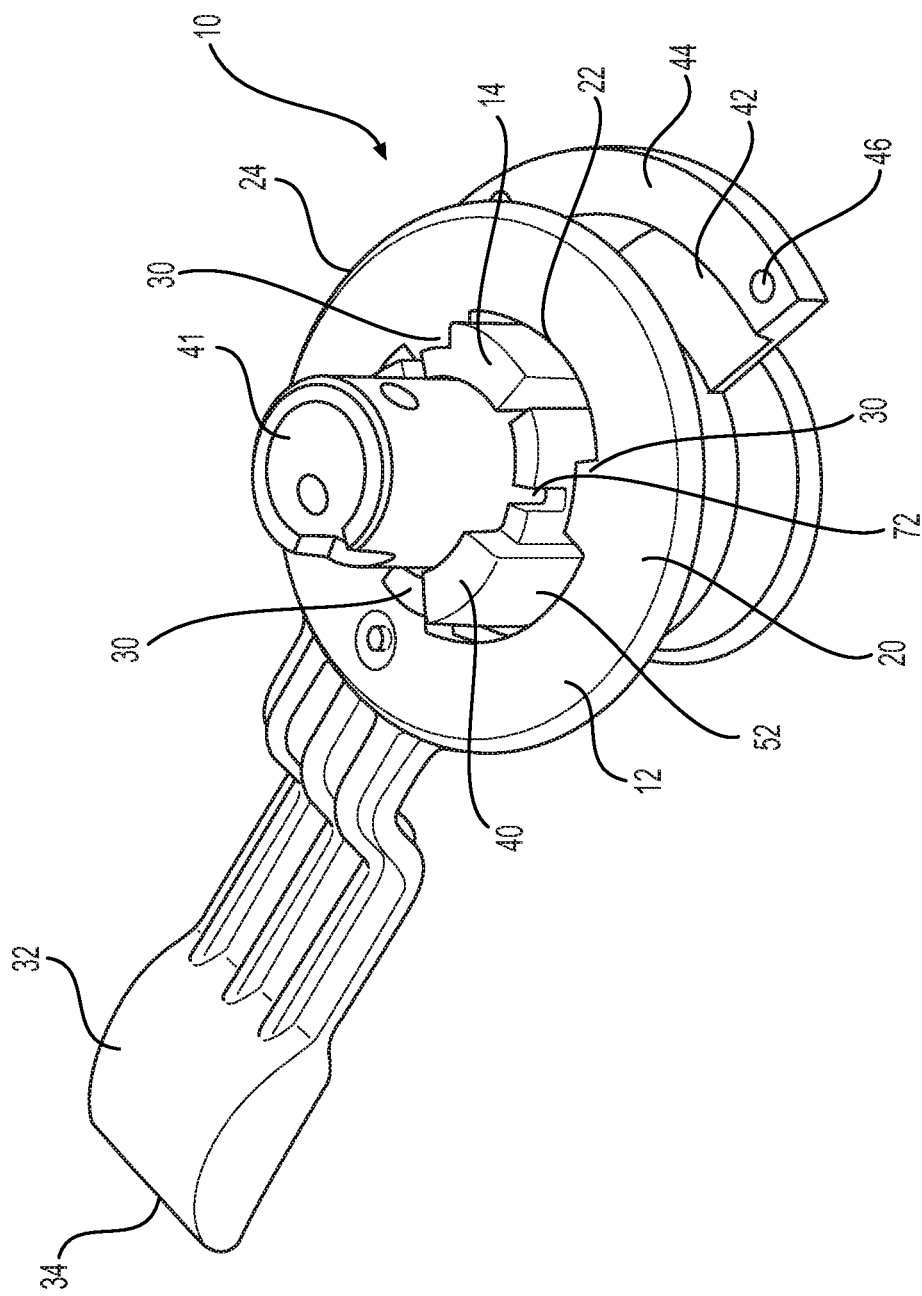
FIG. 2 depicts a perspective view of an exemplary locking mechanism.

FIG. 2 depicts an exemplary brake assembly 10. Brake assembly 10 may include an actuator 12 and a collet 14. Forming an assembly of two components may simplify a locking mechanism for an endoscope, which may reduce costs and complications of manufacturing and/or assembly.

Actuator 12 may include a washer-shaped portion or washer 20 that may have an inner surface 22 and an outer surface 24. Outer surface 24 may have a smooth, annular shape or may have any other suitable shape. Inner surface 22 may have one or more protrusions 30 that are more radially inward than adjacent portions of inner surface 22. As shown in FIGS. 2-5, inner surface 22 may have three protrusions 30. Alternatively, inner surface 22 may have any suitable number of protrusions 30. Use of more protrusions 30 may allow for more braking surface A number of protrusions may match corresponding features of collet 14, described below. Protrusions 30 may have a radially innermost surface that has a curved, concave shape. Alternatively, protrusions 30 may be flat, pointed, convex-curved, or have any other shape, and may be keyed to collet 14, as discussed below.

A lever 32 may extend radially outward from outer surface 24 of washer 20. Lever 32 may be configured to be contacted by a user of an endoscope to rotate actuator 12. As shown in FIG. 2, lever 32 may be cantilevered so that a radially outermost portion 34 of lever 32 may be axially displaced from a plane defined by washer 20. A cantilevered shape of lever 32 may facilitate rotation of actuator 12 by a user exerting a force on lever 32. Lever 32 may alternatively be another type of actuating mechanism such as a knob, rotation mechanism, slider, screw, or other mechanism.

Collet 14 may have a sleeve 40 and a flange 42. Sleeve 40 may have a circular cross-section or a cross-section having a different shape, such as an oval cross-section. A shape of sleeve 40 may be complementary to a shape of an axle 41 of a steering assembly, around which sleeve 40 extends. Collet 14 may be constructed from a compressible material such as plastic. Use of a compressible material may be useful where tolerances are low or to limit friction. Additionally or alternatively, collet 14 may be constructed from a flexible material, such that tabs 50, discussed in further detail below, may be elastically deformed and may have shape memory features.

Figure 3:
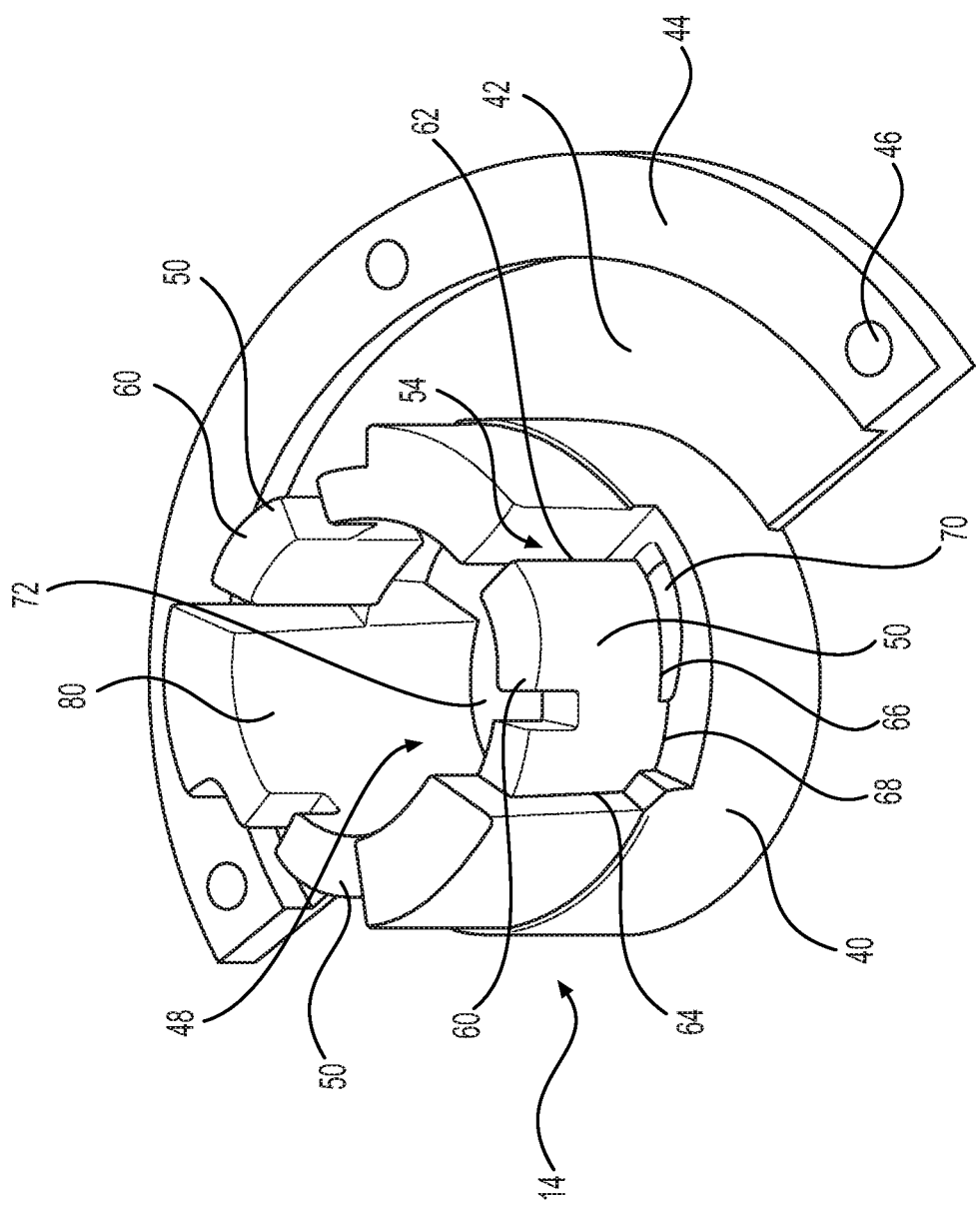
FIG. 3 depicts a perspective view of an exemplary collet of the exemplary locking mechanism.

Flange 42 may extend only partway around an outer circumferential surface of sleeve 40, as shown in FIGS. 2-3. For example, flange 42 may extend halfway or approximately halfway around the outer circumferential surface of sleeve 40. Flange 42 may include a ridge 44 at a radially outer circumferential edge of flange 42. Ridge 44 may serve to restrain one or more components (not shown) of a steering assembly. Ridge 44 may include one or more holes 46, which may be used to secure collet 14 to a handle of an endoscope or to a portion of a steering assembly so that collet 14 may not rotate relative to a handle portion of an endoscope. Collet 14 may be directly or indirectly secured to the handle.

Sleeve 40 may include a longitudinal opening 48 extending from an axially inner surface of collet 14 to an axially outer surface of collet 14. As used herein, an axially inward direction of collet 14 may be a direction toward flange 42. An axially outward direction of collet 14 may be a direction away from flange 42. With particular reference to FIG. 3, sleeve 40 may include one or more tabs 50.

Tabs 50 may be radially inset relative to an outer surface 52 of collet 14. For example, collet 14 may have three tabs 50, as shown in FIGS. 1-4. Tabs 50 may be formed by notches 54 or cut-outs on collet 14, as shown particularly in FIGS. 3-5. For example, notch 54 may be L-shaped, having an axial component and a circumferential component. A number of tabs 50 may be equal to a number of protrusions 30 of actuator 12. Portions of tabs 50 (such as sides of tabs 50 bordered by notch 54, and the axially most-outward side) may be not be directly connected to a remainder of collet 14 and may define free edges. Alternatively, tabs 50 may be formed without notches 54 but may be defined by portions of collet 14 having relatively thinner walls and relatively thicker walls. Other portions of tabs 50 (such as other sides of tabs 50) may be directly fixed to the remainder of collet 14 and may define fixed edges. As shown particularly with respect to FIG. 3, tabs 50 may have at least two free edges, including an axially outward free edge 60 and a radial free edge 62. Axially outward free edge 60 may be an axially outermost side of collet 14. Radial free edge 62 may be parallel to a longitudinal axis of sleeve 40. Tabs 50 may have a radial fixed edge 64. A fourth, axially inward edge 66 of tab 50 may have a fixed portion 68 and a free portion 66. Tab 50 may have a notch 72. Notch 72 may be a groove or an indentation on an axially outermost surface of tab 50/collet 14. Notch 72 may be approximately halfway between radial free edge 62 and radial fixed edge 64. A portion of notch 72 that is closest to fixed portion 64 may be circumferentially aligned with a meeting point of fixed portion 68 and free portion 66.

The free edges/side portions, as well as notch 72 and the material of tab 50, may provide tab 50 with the flexibility to move radially inward and outward, toward and away from opening 48. A portion of tab 50 adjacent to notch 72 may have increased flexibility as compared to other portions of tab 50. For example, a radially inward force exerted on a portion of tab 50 proximate to radial free edge 62 may have a greater effect on tab 50 due to notch 72 than the force would have without the presence of notch 72. Tab 50 may be more easily displaced closer to radial free edge 62 and less flexible closer to radial fixed edge 64. In particular, tab 50 may be less flexible in areas of tab 50 near fixed portion 68.

Tab 50 may be configured so that it is biased into a configuration where radial free edge 62 of tab 50 protrudes radially outward from an inner surface 80 of sleeve 40. Tab 50 is biased radially outward into an at-rest position shown in FIG. 4, but is compressible in a radially inward direction. For example, an inner surface of tab 50 may protrude radially outward relative to an adjacent portion of inner surface 80 of sleeve 40. Alternatively, tab 50 may be biased so that, in an at-rest position, the inner surface of tab 50 is aligned or substantially aligned with inner surface 80, and tab 50 may compressible in a radially inward direction.

Figure 4:
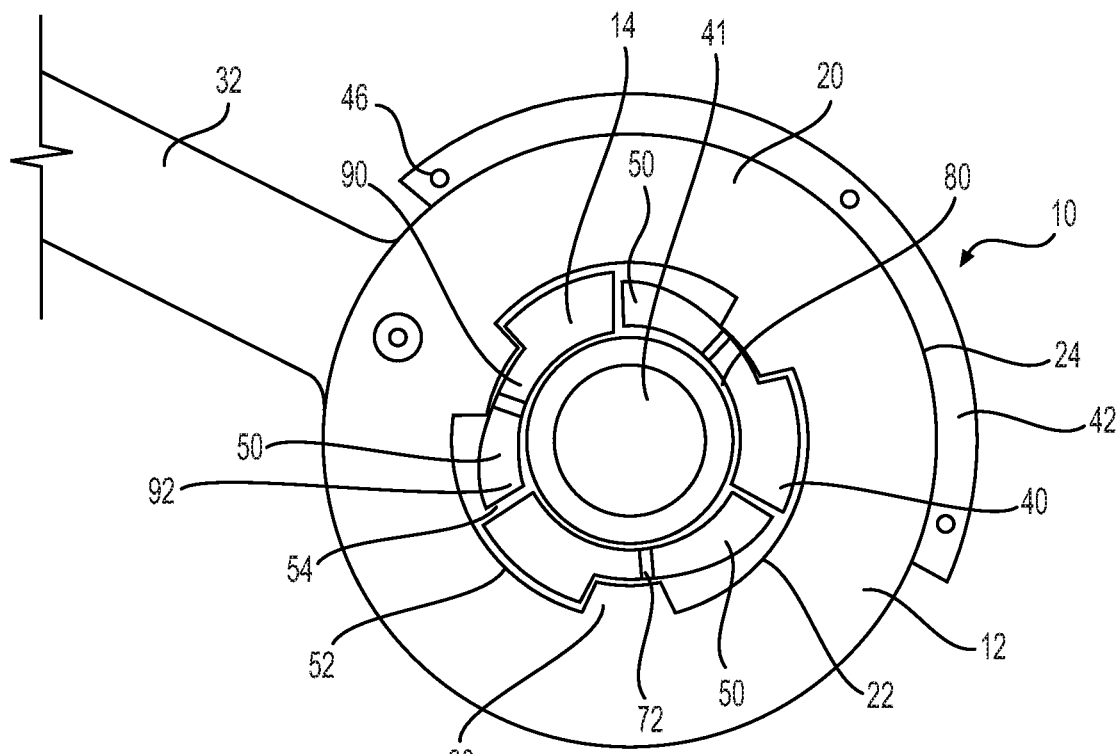
FIG. 4 depicts the exemplary locking mechanism in a first configuration.
Figure 5:
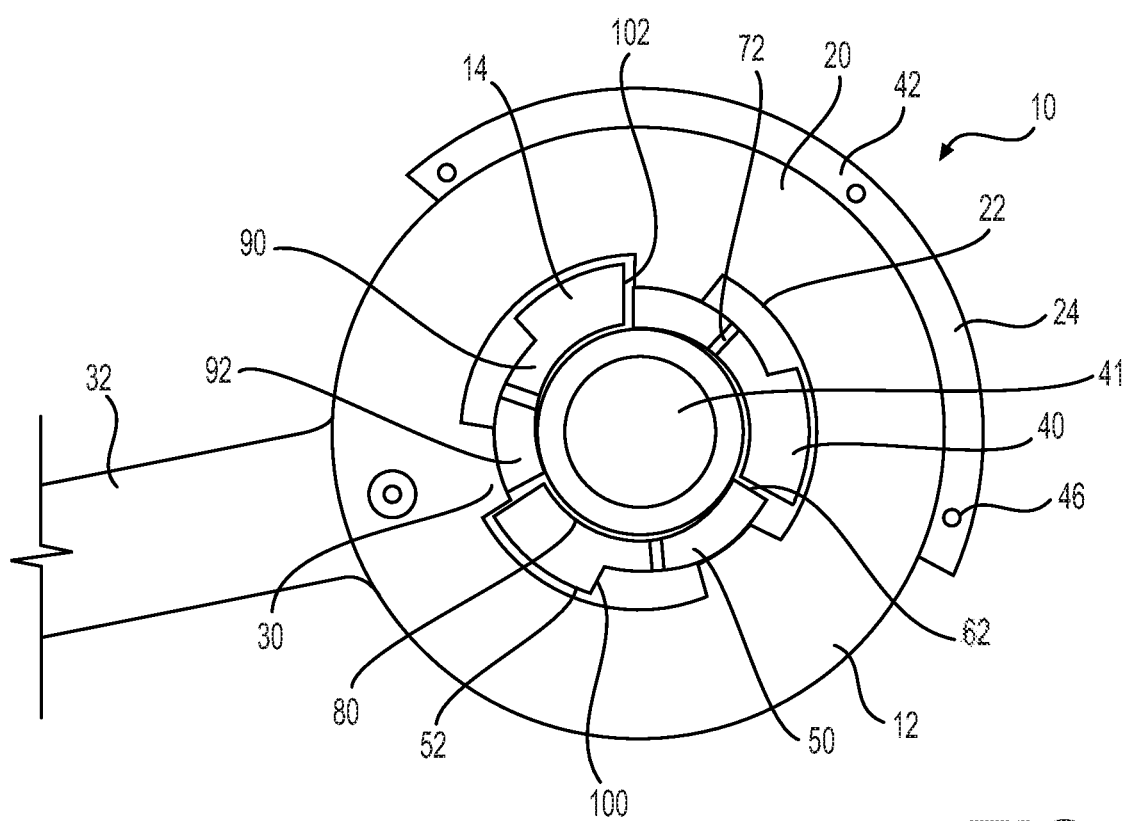
FIG. 5 depicts the exemplary locking mechanism in a second configuration.

As shown in FIGS. 2, 4, and 5, an inner circumferential surface of washer 20 may have a complementary shape to outer surface 52 of sleeve 40. Protrusions 30 of actuator 12 may interact with tabs 50 of collet 14, as discussed below.

Figure 6A:
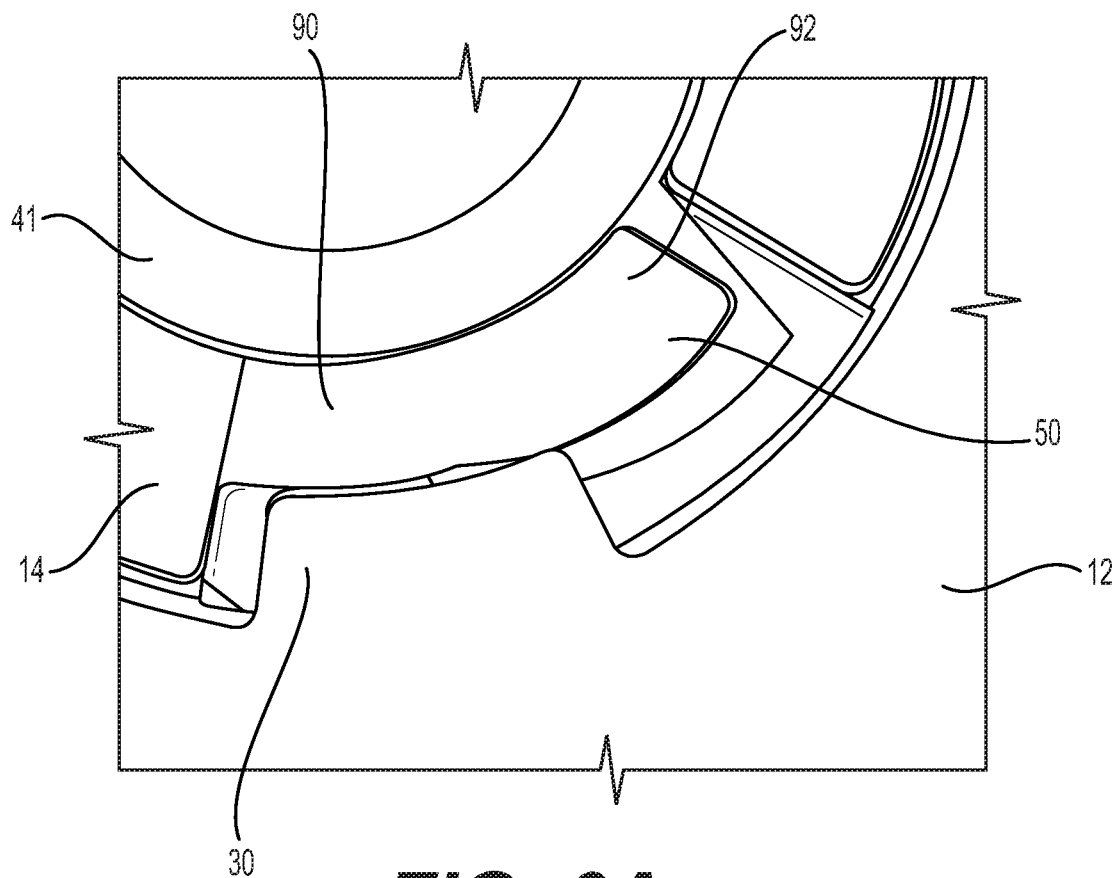
FIGS. 6A-6B show close-up views of the exemplary locking mechanism in the first configuration and the second configuration, respectively.

FIG. 4 shows brake assembly 10 in a first, unlocked configuration. In the first configuration, protrusion 30 may be adjacent to, and radially outside of, a first portion 90 of tab 50 near radial fixed edge 64. FIG. 6A shows a detailed, zoomed-in perspective of a portion of brake assembly 10 in the first, unlocked configuration. Thus, protrusions 30 may not interact with a second portion 92 of tab 50 near radial free edge 62, allowing second portion 92 to project radially outward to the at-rest position, due to, for example, flexure, or an inherent biasing, of tab 50. Alternatively, second portion 92 may be aligned with inner surface 80 of sleeve 40 in the first configuration. Because first portion 90 is proximate to radial fixed edge 64, protrusion 30 may not exert sufficient forces on first portion 90 so as to push first portion 90 into frictional interference with axle 41. For example, FIG. 6A shows a gap between second portion 92 and the axle 41. Fixed portion 68 of axially inward edge 66 may inhibit radially inward displacement of first portion 90 due to protrusion 30 in the first configuration. In the first configuration, axle 41 may be freely rotatable relative to collet 14 because protrusions 30 are not exerting a radial inward force on axle 41 via tabs 50.

Figure 6B:
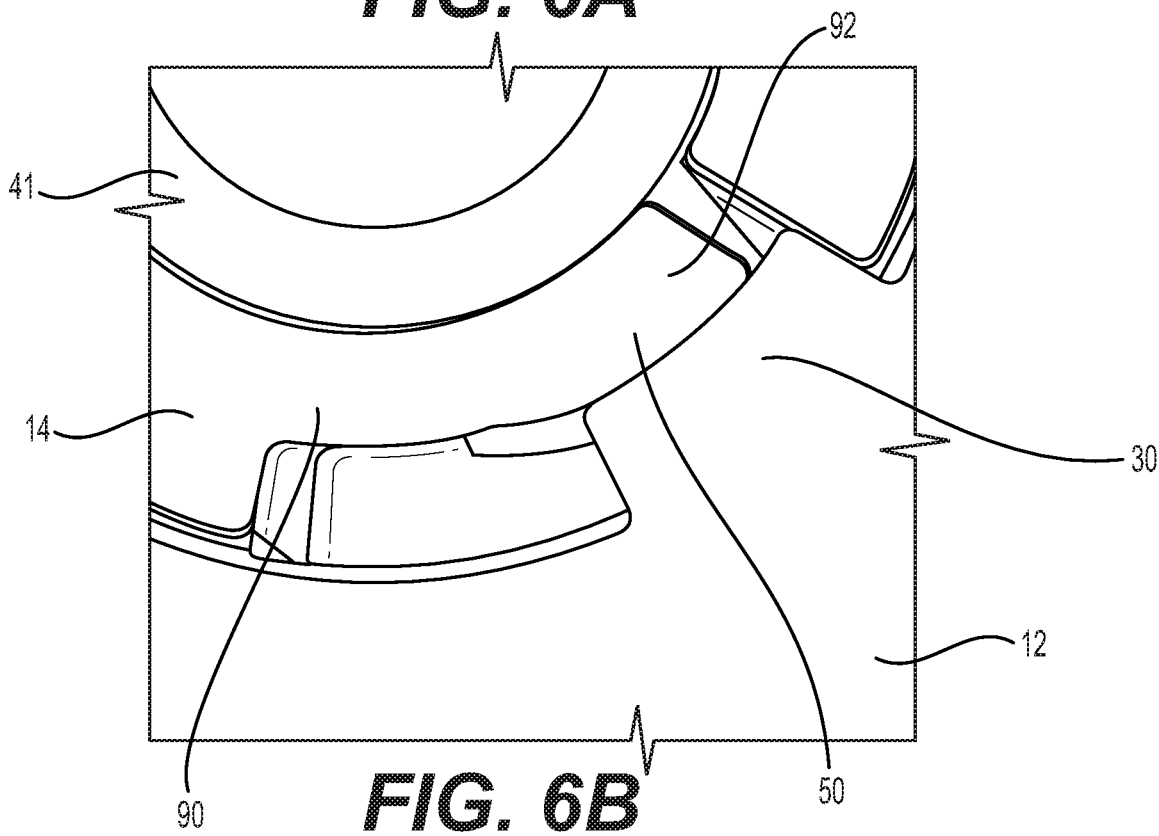

FIGS. 5 and 6B show brake assembly 10 in a second, locked configuration. In the second configuration, protrusion 30 may interact with second portion 92. Second portion 92 may be thicker along a radial direction of collet 14 than other portions of tab 50 so as to facilitate interactions with protrusion 30 in the second configuration. Because second portion 92 has three free sides—axially outward free edge 60, radial free edge 62, and free portion 66 of axially inward edge 66 of tab 50—and because of the material of collet 14, protrusion 30 may exert a force to displace second portion 92 radially inward. For example, protrusion 30 may have 0.0001-0.015 inches of interference, including 0.001-0.007 inches of interference, with tab 50 (e.g., when components of brake assembly 10 are formed of polycarbonate). In the rest position, a radially free edge 62 may extend radially outward past a radially inward edge of protrusion 30. For example, radially free edge may protrude from 0.001 inches to 0.050 inches, including from 0.002 inches to 0.020 inches. A protrusion of radially free edge 62 may serve to retain protrusion 30 (and/or an entirety of actuator 12) in a desired location when brake assembly 10 is in the first configuration such that protrusion 30 (and/or an entirety of actuator 12) does not move or wobble. The numerical values above are exemplary only and may vary depending upon the material used to form components of brake assembly 10.

Thus, in the second configuration, protrusion 30 causes a radially inward force on tab 50. Due to a flexibility of tab 50, second portion 92 may be flexed, or displaced so that second portion 92 is radially inward of inner surface 80 of sleeve 40. A position of first portion 90 may be the same or substantially the same in the first configuration and in the second configuration. Alternatively, first portion 90 may also be displaced, e.g., radially inward, in the second configuration, with respect to the first configuration. In the second configuration, second portion 92 of each tab 50 may be compressed against axle 41. Interference between actuator 12 (e.g., protrusion 30 of actuator 12), tab 50, and axle 41 may produce friction. A frictional force between tabs 50 and axle 41 may inhibit axle 41 from rotating relative to collet 14. The generated friction may also retain actuator 12 in the second configuration of brake assembly 10. Tabs 50 may be formed of a material so as to increase a frictional force. For example, tabs 50 may have a textured surface to increase surface area and/or may include a coating to increase frictional forces. Additionally or alternatively, a surface of axle 41 may be textured or include a coating so as to increase friction.

Actuator 12 may be rotatably movable between the first configuration and the second configuration via lever 32. For example, when brake assembly 10 is in the first configuration, actuator 12 may be moved in a counter-clockwise direction to transition brake assembly 10 to the second configuration. When brake assembly 10 is in the second configuration, actuator 12 may be moved in a clockwise direction to transition brake assembly 10 to the first configuration. Tabs 50 may be resiliently flexible. When brake assembly 10 is transitioned from the second configuration to the first configuration, tabs 50 may transition to an at-rest configuration (projecting radially outward from or aligned with inner surface 80) so that collet 14 does not inhibit rotation of axle 41.

Materials of collet 14 and actuator 12 may be chosen to minimize a force to be exerted by an operator on lever 32 in transitioning collet 14 from the first configuration to the second configuration. A flexibility of tabs 50, compressibility of a material of collet 14, an elasticity of actuator 12/lever 32, an amount of interference between collet 14 and actuator 12, and/or a distance of radial projection of tabs 50 may all affect the force required to actuate lever 32. For example, both collet 14 and actuator 12 may be constructed from high-strength plastic and/or polycarbonate material. Collet 14 and/or actuator 12 may be formed by molding, additive manufacturing, or other manufacturing processes.

Sleeve 40 may include a first step 100 on one radial side of tab 50 and a second step 102 on another radial side or tab 50. For example, first step 100 may be adjacent to radial fixed edge 64, and second step 102 may be adjacent to radial free edge 62 and/or notch 54. Second step 102 may be adjacent to notch 54 and on an opposite side of notch 54 from radial free edge 62. First step 100 and second step 102 may act to limit movement of actuator 12 beyond a desired range of movement. When brake assembly 10 is transitioned from the first configuration to the second configuration, second step 102 may act as a stop to prevent protrusion 30 from moving past second step 102 so that protrusion 30 engages with second portion 92. When brake assembly is transitioned from the second configuration to the first configuration, first step 100 may act as a stop to prevent protrusion 30 from moving past first step 100 so that protrusion 30 is adjacent to first portion 90.

Collet 14 may have interference features, such as surface features, that provide resistance to a user turning knob 230 when brake assembly 10 is in the first configuration. The interference features may provide increased interference when brake assembly 10 is in the second configuration. The interference features may influence how quickly knob 230 may be turned and thus how fast distal end 222 may return to a straight configuration. Interference features may include ridges, protrusions, raised portions, or any other suitable features on collet 14. Alternatively, such interference features may be disposed on a portion of actuator 12.

It will be appreciated that the above elements are merely exemplary. For example, as discussed above, varying numbers of protrusions 30 may be used. Additionally or alternatively to utilizing a frictional relationship to inhibit movement between collet 14 and actuator 12, one or more mechanical features could be employed. For example, collet 14 and actuator 12 may have mating features that align collet 14 and actuator 12 at a selected position. Such features may enable a user to engage brake assembly 10 at selected positions or at selected increments.

Figure 7:
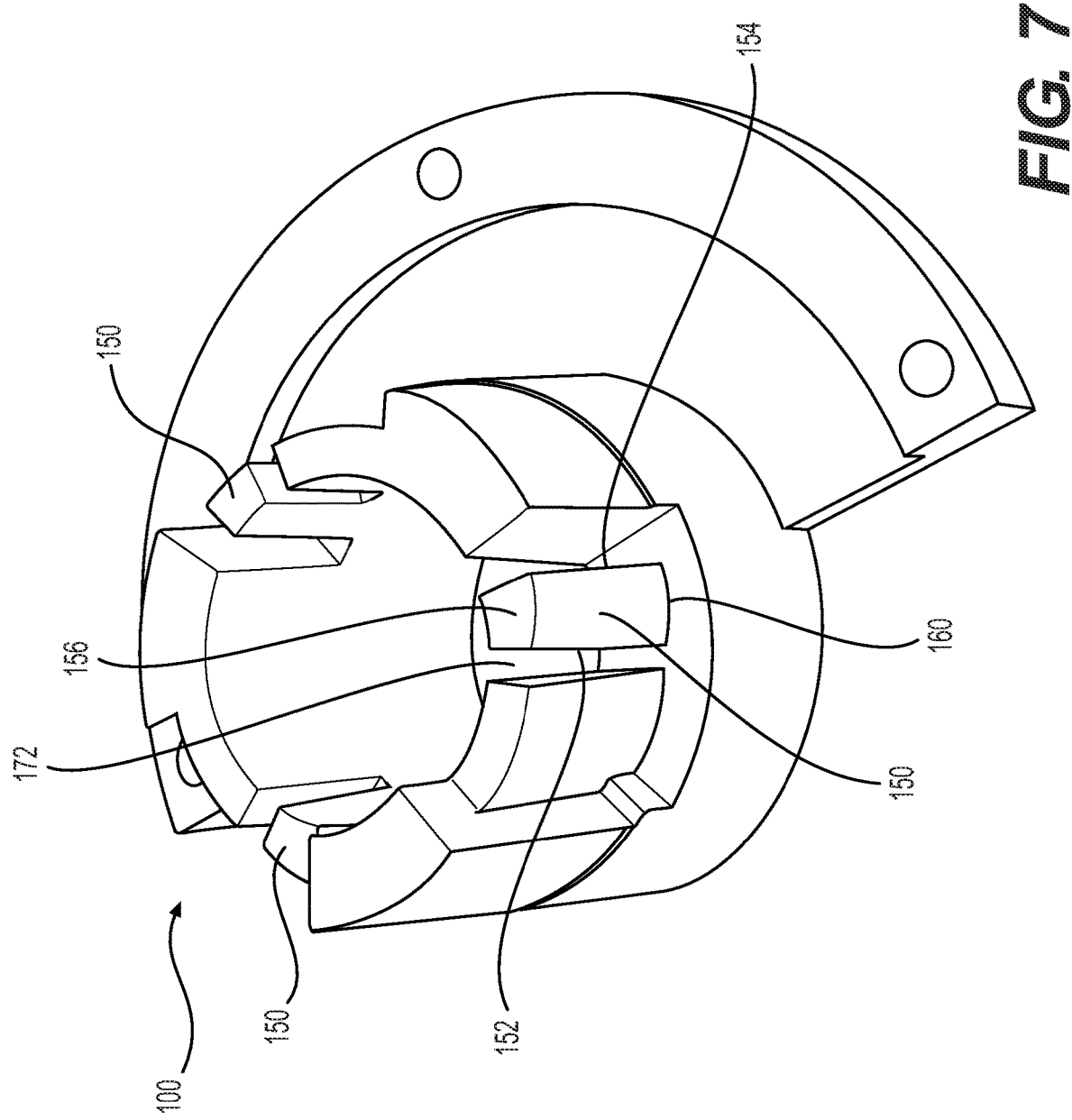
FIG. 7 shows an alternative collet.

FIG. 7 shows an alternative collet 100 that may be used along with actuator 12. Collet 100 may have any of the features of collet 14, described above. Collet 100 may have one or more tabs 150 that extend in an axial direction. A notch 172 may define an edge of tab 150. Notch 172 may have any of the features of notch 72. Although notch 72 may extend only partway through tab 50 in an axial direction, notch 172 may extend along an entirety of tab 150, from an axially proximate portion to an axially distal portion of tab 150. Collet 100 and/or collet 14 may use a combination of tabs 50 and/or tabs 150. Tab 150 may have three free edges and one fixed edge. For example, tab 150 may have a first free radial fixed edge 152, a second free radial edge 154, and a free axial edge 156. Free axial edge 156 may be an axially distalmost edge of collet 100. Tab 150 may have an axial fixed edge 160. Aside from an orientation of tabs 150, collet 100 may function similarly to collet 14 as described above with respect to FIGS. 1-6.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. An assembly comprising:
an axle having an axis of rotation, wherein rotation of the axle about the axis of rotation causes deflection of a portion of a medical device;
a collet having an opening, wherein the axle extends through the opening; and
an actuator configured to interact with the collet, wherein the actuator includes a lever extending radially outward from an outer surface of the actuator and a protrusion extending radially inward from an inner surface of the actuator, toward the axis of rotation;
wherein a first configuration of the collet permits rotation of the axle relative to the collet and a second configuration of the collet inhibits rotation of the axle relative to the collet, wherein, in the second configuration, the actuator is rotated relative to the collet such that the protrusion of the actuator contacts the collet and applies a radially inward force on the collet, toward the axis of rotation, to move a portion of the collet radially inward toward the axis of rotation, and wherein rotation of the actuator relative to the collet transitions the collet from the first configuration to the second configuration.

2. The assembly of claim 1, wherein the collet includes a tab, and the protrusion interacts with the tab to move the tab radially inward, toward the axis of rotation, and transition the collet from the first configuration to the second configuration.

3. The assembly of claim 2, wherein the protrusion is a first protrusion, the actuator further includes a second protrusion and a third protrusion, the tab is a first tab, the collet further includes a second tab and a third tab, and the second protrusion and the third protrusion interact with the second and third tabs, respectively, to transition the collet from the first configuration to the second configuration.

4. The assembly of claim 2, wherein a notch in the collet defines a portion of the tab having a reduced length relative to adjacent portions of the tab.

5. The assembly of claim 2, wherein the tab has a first portion and a second portion, wherein the first portion is less flexible than the second portion.

6. The assembly of claim 5, wherein, in the first configuration, the protrusion is adjacent to the first portion, and, in the second configuration, the protrusion is adjacent to and interacts with the second portion.

7. The assembly of claim 5, wherein the second portion has a greater thickness along a radial direction than the first portion.

8. The assembly of claim 2, wherein the tab is biased to an at-rest position when the collet is in the first configuration, such that a radially-inner surface of the tab is radially aligned with an adjacent portion of the collet or protrudes radially outward from the adjacent portion of the collet.

9. The assembly of claim 1, wherein the actuator includes a washer-shaped portion, and wherein the lever extends radially outward from the washer-shaped portion.

10. The assembly of claim 1, wherein the collet includes a sleeve, and a flange extending circumferentially around at least a portion of the sleeve.

11. The assembly of claim 1, wherein the collet includes a stop configured to prevent movement of a portion of the actuator past the stop.

12. A locking assembly comprising:
   a collet having a tab; and
   an actuator having a protrusion extending radially inward, toward an axis of rotation of the actuator, from an inner surface of the actuator and a lever extending radially outward, away from the axis of rotation of the actuator, from an outer surface of the actuator;
   wherein the actuator is rotated such that the protrusion of the actuator interacts with the tab to move the tab radially inward toward the axis of rotation of the actuator in order to transition the collet from a first configuration to a second configuration, wherein, in the first configuration of the collet, an axle is rotatable to deflect a portion of a medical device, and, wherein, in the second configuration of the collet, the axle is not rotatable due to a frictional force applied to the axle by the tab in a radially inward direction toward the axis of rotation of the actuator.

13. The locking assembly of claim 12, wherein the actuator includes a washer-shaped portion that defines the inner surface of the actuator, and wherein the protrusion extends from the inner surface of the washer-shaped portion.

14. The locking assembly of claim 12, wherein the tab is biased to an at-rest position that is radially aligned with an adjacent portion of the collet or protrudes radially outward from the adjacent portion of the collet.

15. A locking assembly comprising:
   an axle, wherein rotation of the axle causes deflection of a sheath of a medical device;
   a collet having a sleeve portion, wherein the axle extends through a central opening of the sleeve portion, and wherein the sleeve portion has a flexible tab; and
   an actuator having a washer-shaped portion radially outward, away from a central longitudinal axis of the axle, of the sleeve portion of the collet, wherein the actuator includes a protrusion extending radially inward, toward the central longitudinal axis of the axle, from an inner surface of the washer-shaped portion, and a lever that extends radially outward, away from the central longitudinal axis of the axle, from an outer surface of the washer-shaped portion;
   wherein the protrusion is adjacent to at least a portion of the flexible tab, and wherein the actuator rotates relative to the collet so that the protrusion applies a radially inward force, toward the central longitudinal axis of the axle, on the flexible tab such that the tab moves radially inward, toward the central longitudinal axis of the axle, to interact with and prevent rotation of the axle.

16. The locking assembly of claim 12, wherein the tab is flexible.

17. The assembly of claim 1, wherein a portion of the collet includes an outward-facing wall and an inward-facing wall,
   wherein, in the second configuration, the actuator is rotated relative to the collet such that the radially inward force from the actuator is applied to the outward-facing wall of the collet to move the portion of the collet radially inward toward the central longitudinal axis of the axle, and
   wherein, in the second configuration, an inward-facing wall of the portion of the collet applies a radially inward force on the axle to inhibit rotation of the axle relative to the collet.

18. The assembly of claim 1, wherein the collet is configured to be secured to a handle of a medical device.

19. The locking assembly of claim 15, wherein the collet is configured to be secured to a handle of the medical device.

20. The locking assembly of claim 15, wherein the collet includes a flange extending circumferentially around at least a portion of the sleeve portion, and wherein the washer-shaped portion of the actuator rotates around the sleeve portion and between the sleeve portion and an outermost edge of the flange.

* * * * *